United States Patent [19]
Nakayama et al.

[11] 4,182,167
[45] Jan. 8, 1980

[54] YARN TENSION METER

[75] Inventors: Takao Nakayama, Otsu; Chikayasu Yamazaki, Kyoto; Michio Ohno, Otsu, all of Japan

[73] Assignee: Toray Industries, Inc., Tokyo, Japan

[21] Appl. No.: 940,352

[22] Filed: Sep. 7, 1978

[51] Int. Cl.² ............................................. G01L 5/10
[52] U.S. Cl. .................................................... 73/144
[58] Field of Search .................. 73/144, 143; 242/45, 242/147 R, 147 A, 147 M, 148

[56] References Cited
U.S. PATENT DOCUMENTS

| | | | |
|---|---|---|---|
| 3,994,162 | 11/1976 | Auckland et al. | 73/144 |
| 4,092,857 | 6/1978 | Lawson | 73/144 |

*Primary Examiner*—Jerry W. Myracle
*Attorney, Agent, or Firm*—Miller & Prestia

[57] ABSTRACT

A yarn tension meter comprising a tension detecting unit, a rotary guide, at least one force transducer and fixed guides which, without damaging a running yarn, permits measurement of tension values of the yarn with a high degree of accuracy.

6 Claims, 11 Drawing Figures

YARN TENSION METER

FIELD OF THE INVENTION

The present invention relates to a yarn tension meter which is employed in the textile industry for measurement of the tension of yarn running at high speed. The meter is useful in the process of manufacture and/or inspection of textile products, for the purpose of ascertaining and determining manufacturing and/or testing conditions to be applied in such processes.

DESCRIPTION OF THE PRIOR ART

Means for measuring the tension of running yarn such as those shown in FIGS. 1 and 2, have hitherto been known.

The yarn tension meter as shown in FIG. 1 comprises a force transducer 7 which is provided with an elastic plate 5 with one end fastened and a guide 4 located at its other end. Fixed yarn guides 2 and 3 are provided at locations spaced from the force transducer 7.

When a yarn 1 runs in a predetermined path as illustrated, the guide 4 of the force transducer 7 is biased in the direction of the arrow "a" and adds strain to the elastic plate 5. Such strain is converted, by a strain gauge circuit including a strain gauge 6 and a signal processor 8, into a signal indicative of the tension of the yarn, and the tension value is indicated on a meter 9.

A conventional meter like this has drawbacks owing to the fact that the yarn 1 is constantly in touch with the fixed guides 2 and 3, and with the guide 4 of the force transducer 7. Such drawbacks include:

(1) Frictional resistance to which the running yarn is subjected because of contact with guides 2, 4 gives rise to a tension loss in the yarn. Hence, it is impossible to obtain a high degree of accuracy.

(2) Frictional resistance causes damage to the running yarn. When the yarn runs at high speed, in particular, heat is generated by the frictional resistance, and this gives rise to yarn breakage.

The yarn tension meter as shown in FIG. 2 is, on the other hand, provided with a vibrator 10 to which the fixed end of the elastic plate 5 of FIG. 1 is attached.

When the elastic plate 5 is vibrated using the vibrator 10 of FIG. 2, the elastic plate 5 reciprocates between the positions indicated by solid and dotted lines, and the measurement of tension values becomes intermittent. Damage done to the yarn accordingly becomes intermittent as well, and the amount of heat generated is reduced to a certain extent. However, this is not enough to eliminate harmful effects on the yarn in many cases. Further, tension meters of this type have the following drawbacks:

(1) When measuring tension, just as in FIG. 1 it is impossible to ensure a high degree of accuracy.

(2) As the elastic plate 5 is vibrated, the wiring between the strain gauge 6 and the signal processor 8 is subject to damage.

(3) Since the tension signals from the strain gauge 6 are joined by signals caused by vibration of the elastic plate 5, a high degree of accuracy cannot be obtained.

SUMMARY OF THE INVENTION

The object of the present invention is to provide a yarn tension meter which eliminates the drawbacks of the conventional techniques and permits measurement of tension values of a running yarn with a high degree of accuracy and without causing damage to the yarn.

The tension meter of the present invention is provided with a rotary guide driven by a motor and includes at least one force transducer for detection of contact pressure of the yarn as an electric signal. It also includes fixed guides which determine the running course of the yarn. The force transducer is disposed between the rotary guide and the fixed guides, thus attaining the advantages of the present invention, as will further become apparent hereinafter and in the drawings.

DETAILED DESCRIPTION OF PREFERRED EMBODIMENTS

Details of the embodiments of the present invention will be described with reference to the drawings. It is to be understood, however, that the present invention is not confined to these embodiments.

Figure 1:
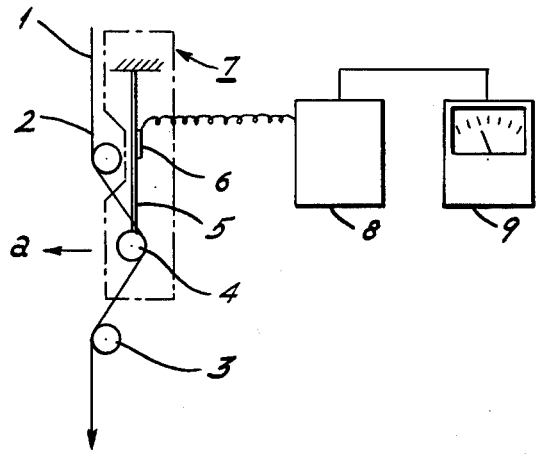
FIGS. 1 and 2 are schematic representations of conventional tension meters, and show techniques heretofore employed.
Figure 2:
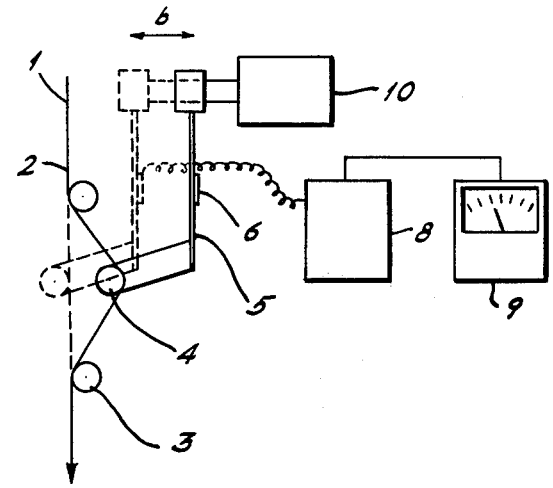
Figure 3:
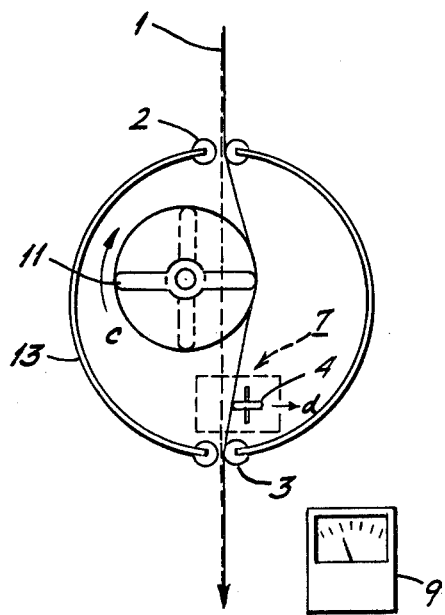
FIG. 3 is a schematic front view of a yarn tension meter embodying features of the present invention, with the dash lines representing alternative positions of the yarn and of the element 11 thereof.
Figure 4:
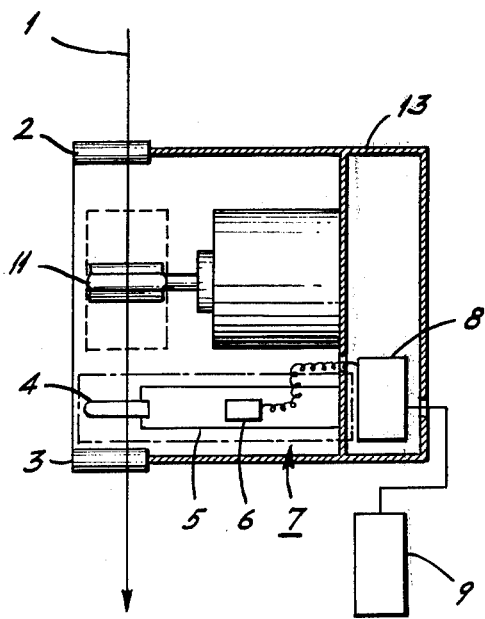
FIG. 4 is a side view of the yarn tension meter shown in FIG. 3.

FIGS. 3 and 4 show an embodiment of a yarn tension meter according to the present invention. In these figures, the number 1 indicates a running yarn, and members 2 and 3 are fixed guides which are fastened to a casing 13. A force transducer 7 contains an elastic plate 5 (FIG. 4) with a strain gauge 6 attached thereto. One end of elastic plate 5 is fastened to the casing 13 and the other end is attached to a guide 4. The number 8 designates a signal processor, 9 a meter, and 11 a rotary guide having legs 180° apart, which legs are driven by a motor 12 and which cause the yarn 1 to pulsate between the fixed guides 2 and 3.

Since the measurement of tension of the running yarn is effected by the yarn 1 urging the guide 4 in the direction of the arrow "d" when the rotary guide 11 is urged against the yarn in the position indicated by solid lines, the fixed guide 2 may be omitted if desired.

When the legs of the rotary guide 11 are rotated in the direction of the arrow "c", the yarn 1 is pulsated between the position indicated by the solid line and that indicated by the dash line, and pressure is intermittently applied to the guide 4 by the yarn.

When the guide 4 receiving a pulse from leg 11 is thus biased the strain gauge 6 detects the resulting force and signals it through the signal processor 8 into the meter 9, where it is indicated as a tension value.

Figure 5:
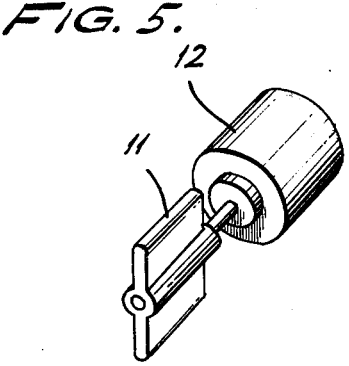
FIGS. 5, 6 and 7 are views in perspective showing different shapes of rotary guides used in yarn tension meters according to the present invention.
Figure 6:
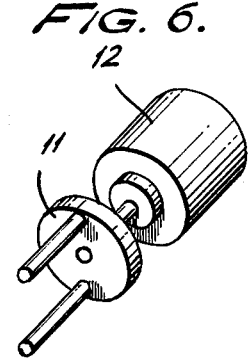
Figure 7:
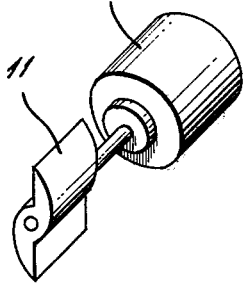

FIGS. 5, 6 and 7 show different shapes of the rotary pulsing device. In FIG. 5 the rotator is a platelike body consisting of a rotating shaft and having two blades fixed on the shaft. FIG. 6 shows a rotator in the form of a circular plate with two guide pins projecting from its surface and the circular plate is fixed on an end of a rotating shaft at its center. In FIG. 7 the rotator is formed at two curved yarn guide surfaces on a cam. In any event, the rotary guide can be of any desired shape or type, so long as it is provided, around the axis of its rotating shaft, with a pulsating yarn guide surface driven by the shaft.

Figure 8:
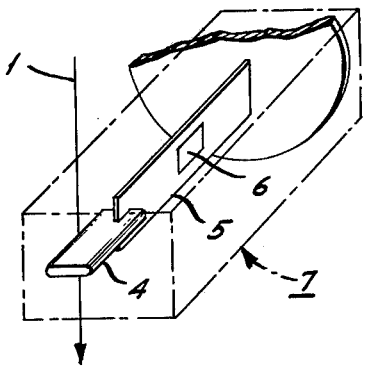
FIGS. 8 and 9 are views in perspective showing different structures of the force transducer.
Figure 9:
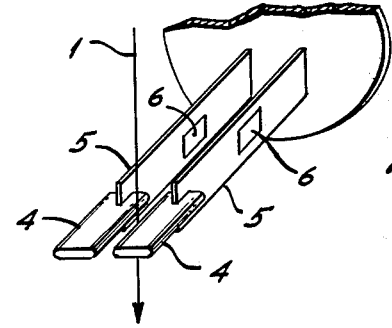

FIGS. 8 and 9 show selected examples of the types of force transducers that may be used. In FIG. 8 only one force transducer is provided. In FIG. 9 two force transducers 7 are provided. Under ordinary circumstances a tension meter having only one force transducer 7 will serve the purpose. When, however, measurement is to be carried out at places where vibrations and temperature fluctuations are encountered, a yarn tension meter having two force transducers 7 may be used to best advantage. In this instance, one force transducer detects the tension of the yarn and also detects the vibrations, while the other transducer is caused to detect only the vibrations (not being brought into contact with the yarn). The signal is imposed upon a bridge circuit, with the utilization of strain gauges in the force transducers. By this means, the effect of temperature fluctuations and vibrations can be eliminated and pure tension signals can be obtained.

Figure 10:
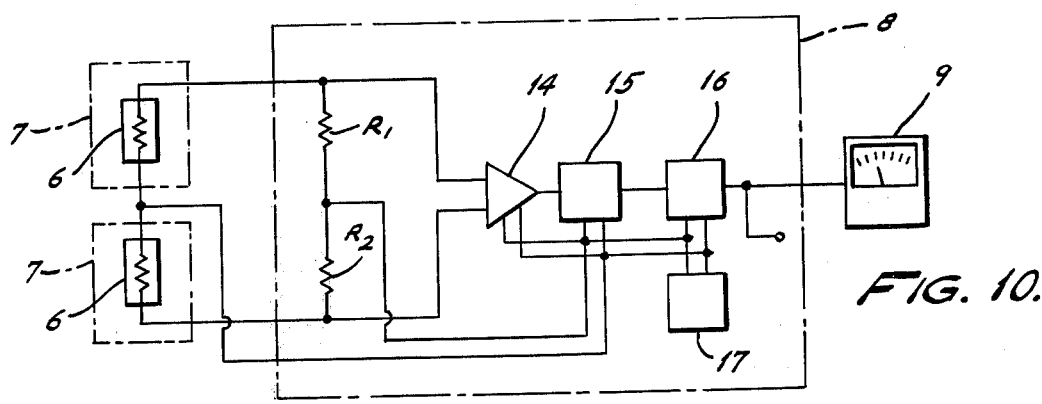
FIG. 10 is a block diagram showing, as one example, the composition of a circuit designed to accept a tension signal detected by strain gauges and indicate it as a tension value.

FIG. 10 shows an example of a signal circuit when tension measurement is carried out by the use of a yarn tension meter in which a combination of two force transducers 7, 7 is employed. By virtue of the fact that two strain gauges 6 are used, a bridge is formed by circuits including resistances $R_1$ and $R_2$ in the signal treatment circuit. The resistances of strain gauges 6, 6 vary with yarn tension. The bridge output is amplified by an amplifier 14 and is fed into a band elimination filter 15. The output of the band elimination filter 15 is fed into a peak detector circuit 16, and its output is in turn fed into the meter 9, and is there indicated as a tension value. The number 17 indicates the power supply.

Figure 11:
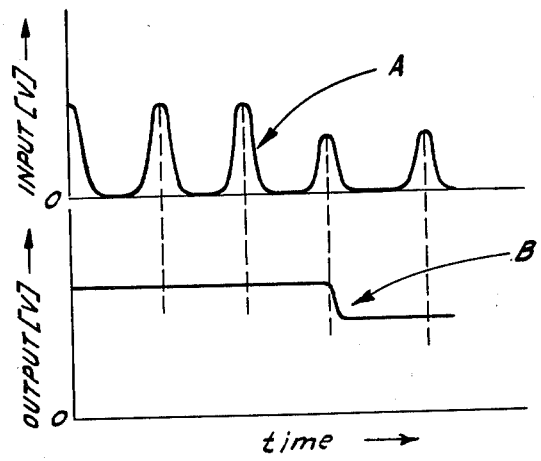
FIG. 11 is a diagram showing the relationship between two signals obtained by the circuit shown in FIG. 10.

FIG. 11 is a voltage-time diagram showing the relationship between the input and output signals of the peak detector circuit 16 as shown in FIG. 10. In this diagram, the curve "A" indicates the input signal of the peak detector circuit, and its peak values show the tension of the yarn measured intermittently in response to the pulsations of the (rotary) pulsing guide. The curve "B" shows, on the other hand, the output signal of the peak detector circuit, retaining the peak values of the curve "A". Such retained values are indicated on the meter as the tension values of the yarn.

Having described selected embodiments of the present invention with reference to the drawings, important effects brought about in accordance with this invention will now be described as follows.

Since a tension meter of the present invention is so composed that its tension detection unit comprises a rotary guide, at least one force transducer and fixed guides, it has many advantages, including those described below. (1) The intermittent measurement of the tension of a running yarn can be easily attained. (2) As the (rotary) pulsing guide is rotated in the same direction as the running direction of the yarn, frictional resistance arising from the contact between the pulsing guide 11 and the yarn can be kept to a minimum. Further, the amount of movement of the guide 4 is very small, and the amount of frictional resistance arising from contact of the yarn with the fixed guide 3 is also very small. Furthermore, since the fixed guide 2 may be done away with if desired, the frictional resistance arising from contact between the yarn and the guides is essentially limited to friction resulting from contact of the yarn with the guide 4. Consequently, the amount of frictional resistance which the yarn tension meter applies to the yarn at the time of tension measurement is very small; hence no damage is caused to the yarn.

(3) When the amount of frictional resistance at the guides is reduced, the tension loss from frictional resistance at each guide is also reduced. This allows significant improvement in the accuracy of the measured tension values.

We claim:

1. A yarn tension meter for measuring the tension of a running yarn comprising:
    (a) a rotary guide having a yarn guide surface fixed on a rotating shaft, said shaft being driven by a motor;
    (b) at least one force transducer for detection of contact pressure of the yarn on said yarn guide surface as an electrical signal; and
    (c) fixed guide means arranged to provide a predetermined path for the running yarn;
said force transducer being disposed between said rotary guide and said fixed guide means.

2. A yarn tension meter as claimed in claim 1, wherein said rotary guide includes a plurality of blades fixed on said rotating shaft.

3. A yarn tension meter as claimed in claim 1, wherein said rotary guide consists of a circular plate fixed on an end of said shaft and a plurality of guide pins fixed on said circular plate and extending around the rotation axis of the plate.

4. A yarn tension meter as claimed in claim 1, wherein said rotary guide is a cam having a plurality of curved yarn guide surfaces.

5. A yarn tension meter as claimed in claim 1, wherein said force transducer comprises an elastic plate, a strain gauge attached to said elastic plate, and a guide fixed to an end of said elastic plate.

6. A yarn tension meter as claimed in claim 1, wherein units of force transducers are provided in a common circuit.

* * * * *